(12) United States Patent
Betts et al.

(10) Patent No.: US 10,537,070 B2
(45) Date of Patent: Jan. 21, 2020

(54) PROCESS FOR THE PRODUCTION OF MYCELIAL COMPOSITE SURFACES IN A ROLL-TO-ROLL FORMAT

(71) Applicants: Jeffrey Daniel Betts, Newtown, PA (US); Gregory John Tudryn, Hadley, MA (US); Courtney Elizabeth Hart, Adams, MA (US)

(72) Inventors: Jeffrey Daniel Betts, Newtown, PA (US); Gregory John Tudryn, Hadley, MA (US); Courtney Elizabeth Hart, Adams, MA (US)

(73) Assignee: Ecovative Design LLC, Green Island, NY (US)

( * ) Notice: Subject to any disclaimer, the term of this patent is extended or adjusted under 35 U.S.C. 154(b) by 597 days.

(21) Appl. No.: 15/099,790

(22) Filed: Apr. 15, 2016

(65) Prior Publication Data

US 2016/0302365 A1 Oct. 20, 2016

Related U.S. Application Data

(60) Provisional application No. 62/147,813, filed on Apr. 15, 2015.

(51) Int. Cl.
*C12N 1/14* (2006.01)
*A01G 18/00* (2018.01)

(52) U.S. Cl.
CPC .................................. *A01G 18/00* (2018.02)

(58) Field of Classification Search
CPC .......... A01G 1/04; A01G 18/00; A01G 18/20; A01G 18/50; A01G 18/61; C12R 1/645
USPC ............................................ 47/1.1; 435/254.1
See application file for complete search history.

(56) References Cited

U.S. PATENT DOCUMENTS

| 4,265,915 A * | 5/1981 | MacLennan | A23J 3/20 |
| | | | 426/28 |
| 5,589,390 A * | 12/1996 | Higuchi | A01G 13/10 |
| | | | 424/403 |
| 8,298,810 B2 * | 10/2012 | Rocco | B01F 5/0212 |
| | | | 435/174 |
| 9,879,219 B2 * | 1/2018 | McIntyre | C12N 1/14 |
| 2012/0270302 A1 * | 10/2012 | Bayer | C12N 1/14 |
| | | | 435/254.1 |

* cited by examiner

*Primary Examiner* — Peter M Poon
*Assistant Examiner* — Danielle A Clerkley
(74) *Attorney, Agent, or Firm* — Francis C. Hand; Carella, Byrne, Et Al

(57) ABSTRACT

A method of producing a mycological composite material comprises inoculating a substrate of fibrous material with an inoculum of mycelial tissue; rolling the inoculated substrate into a roll; and thereafter incubating the rolled inoculated substrate for a time sufficient for the mycelial tissue to grow hyphae that enmesh with the substrate to form a cohesive unified filamentous network with the rolled inoculated substrate being characterized in being flexible. The rolled inoculated substrate may be subsequently processed by subjecting lengths of the roll to heat and pressure in molds to form rigid products.

18 Claims, 4 Drawing Sheets

Figure 1:
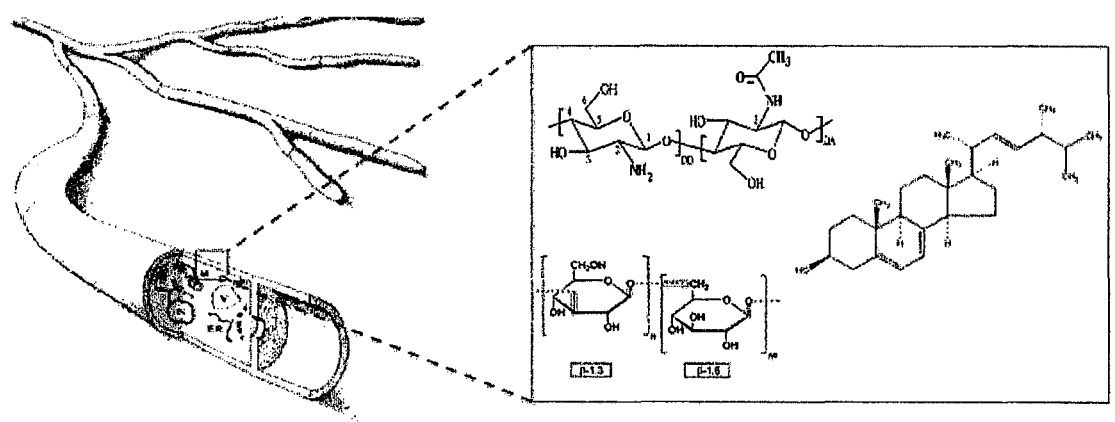

PROCESS FOR THE PRODUCTION OF MYCELIAL COMPOSITE SURFACES IN A ROLL-TO-ROLL FORMAT

This application claims the benefit of U.S. Provisional Patent Application No. 62/147,813, filed Apr. 15, 2015.

This invention relates to a process for the production of mycelial composite surfaces in a roll-to-roll format. More particularly, this invention relates to a process for the production of flexible and rigid mycelial composite surfaces in a roll-to-roll format.

BACKGROUND

Published US Patent Application 2015/0101509 discloses a method of making a composite body employing chitin and glucan-containing mycelia cells and discrete particles wherein a mass of material made up of the chitin and glucan-containing mycelia cells and discrete particles is compressed under heat and compression for a time sufficient to allow cross-linking between the cellular matrix in the mycelia cells to bind the discrete particles together in the compressed body.

Generation of mycelial tissue throughout a woven, or non-woven lignocellulosic, saccharide, or synthetic matrix offers the ability to produce a uniform or non-uniform distribution of biomass that can be used for enhancing or targeting physical properties of a biological composite material prepared in a rolled format. Distribution of the fungal network provides a variety of intra or extracellular matrix components in fungal tissue that may act as a resin during a post-growth activation, or catalyzed process.

Compounds that are often associated with the fungal cell wall include chitin, chitosan, β-glucan, proteins, minerals, and other polysaccharides When exposed to sufficient heat, moisture, or other catalyst, these have the potential to flow, contact, fuse and/or form covalent, physical, or ionic cross-links throughout the material.

A network of mycelial tissue proliferated across and throughout a fibrous, high flexibility or low-flexibility substrate, can be accessed or activated in a variety of ways to modify the physical characteristics of the fungal cell wall components and subsequently the bulk properties of the biomaterial. This practice proposes preparation, distribution, and activation pathways upon the extracellular (and/or intracellular) fungal cell saccharides, and other macro and micromolecular components.

OBJECTS OF THE INVENTION

It is an object of the invention to provide a relatively simple process for the production of mycelial composite surfaces in a roll-to-roll format.

It is another object of the invention to provide a mycological composite in rolled format.

BRIEF SUMMARY OF THE INVENTION

Briefly, the invention provides a method of producing a mycological composite material and a mycological composite material made thereby.

In one embodiment, the method of producing a mycological composite material includes the steps of forming an inoculum of mycelial tissue; of inoculating a substrate of fibrous material with said inoculum; of rolling the inoculated substrate into a roll; and thereafter incubating the rolled inoculated substrate for a time sufficient for the mycelial tissue to grow hyphae that enmesh with the substrate by extending around the fibers of the substrate to form a cohesive unified filamentous network with the rolled inoculated substrate being characterized in being flexible.

The step of inoculating may be conducted by deposition of the inoculum on a surface of the substrate. For example, where the inoculum is in the form of solid particles, the inoculum is deposited under gravity onto the substrate of fibrous material and where the inoculum is in the form of a liquid, the inoculum is sprayed onto the substrate of fibrous material. In addition, the substrate may be conveyed in a continuous manner during deposition of the inoculum on the surface of the substrate.

Alternatively, the step of inoculating may be conducted by conveying the substrate of fibrous material through a bath of said inoculum.

After inoculation, the incubated substrate may be rolled up on itself or may be co-rolled with a support web of porous material into a composite roll of alternating layers (or convolutions) of substrate and porous material. Thereafter, the composite roll is dehydrated to below 20% moisture and ideally below 8% for storage and/or transportation to another site for further processing. In this condition, the incubated substrate is flexible.

The term "flexible" means that the rolled substrate may be unrolled, for example, into a flat web or sheet while retaining the integrity of the incubated substrate.

In accordance with the invention, the mycelial tissue of the inoculum contains chitin and glucan-containing mycelial cells. Thus, in order to further process the rolled inoculated substrate, a length of the incubated substrate is unrolled from the rolled substrate and subjected to heat and pressure sufficient to cause the glucan-containing mycelial cells therein to bond said length into a rigid structure.

In order to prepare the composite roll of alternating layers of substrate and porous material, a flow of moisture is passed through the layers of porous material into the layers of substrate to re-hydrate the layers of substrate to between 30% and 70% moisture.

Alternatively, where a length of the incubated substrate is unrolled from the rolled substrate and subjected to heat and pressure, a flow of steam may be passed through the layers of porous material into the layers of substrate to re-hydrate the layers of substrate.

The invention also provides a mycological composite material in the form of a web of mycelial tissue impregnated fibrous material characterized in being flexible and wherein the mycelial tissue contains chitin and glucan-containing mycelial cells.

In one embodiment, the mycological composite material is in the form of a roll with a web of porous material disposed in alternating layers the fibrous material.

The method described here can be applied to any species of fungi and tailored to yield the desired extent, or combination of modifications thereof.

Figure 2:
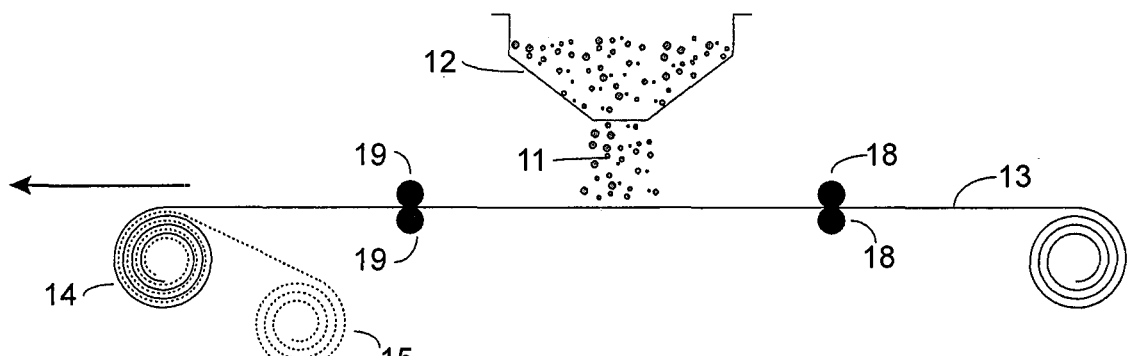
Figure 3:
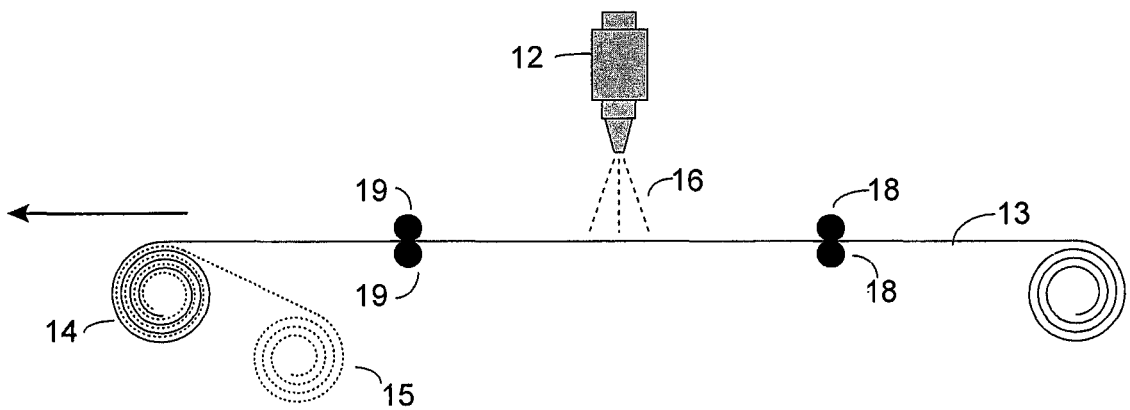
Figure 4:
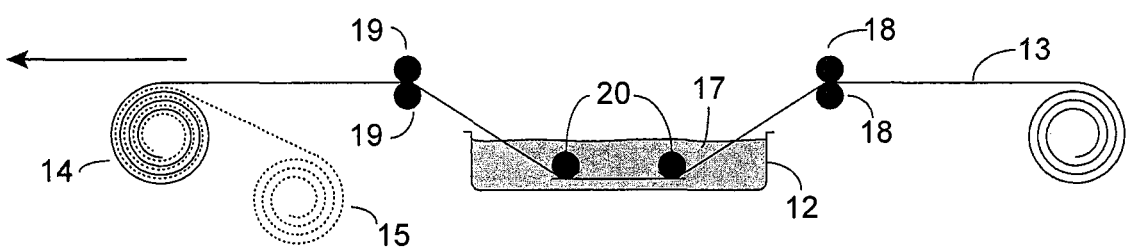
Figure 5:
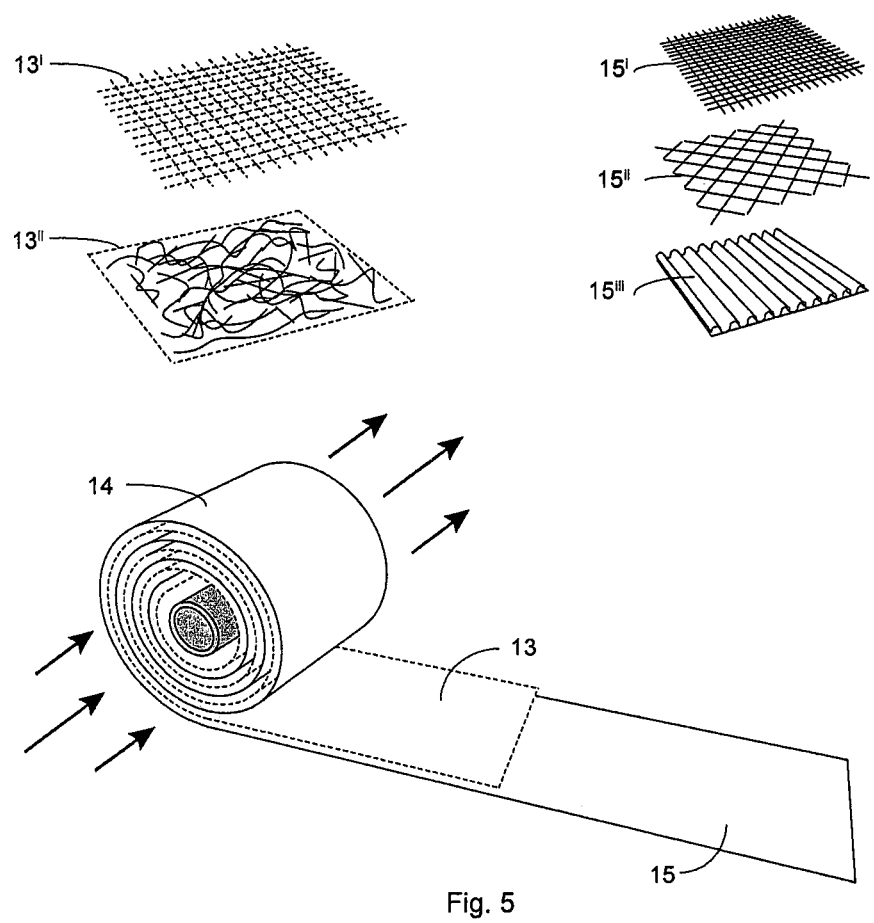
Figure 6:
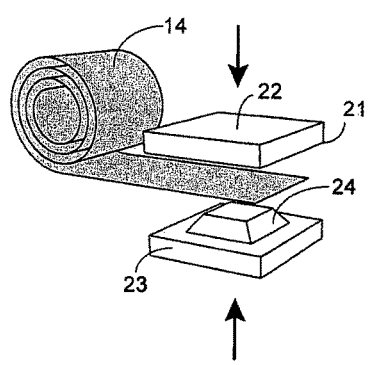
Figure 7:
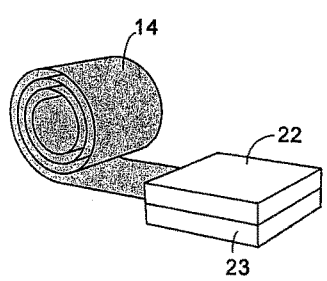
Figure 8:
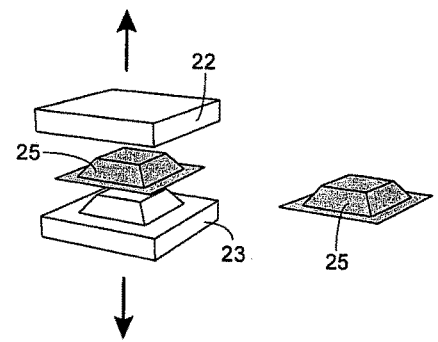
Figure 9:

These and other objects and advantages of the invention will become more apparent form the following detailed description taken in conjunction with the accompanying drawings wherein:

FIG. 1 illustrates an image of a fungal cell wall and a deconstructed section of the cell wall with intracellular chitin and structural saccharides;

FIG. 2 schematically illustrates an apparatus for depositing an inoculum under gravity onto a travelling web of fibrous substrate in accordance with the invention;

FIG. 3 schematically illustrates an apparatus for depositing an inoculum by spraying onto a travelling web of fibrous substrate in accordance with the invention;

FIG. 4 schematically illustrates an apparatus for passing a travelling web of fibrous substrate through a bath of inoculum in accordance with the invention;

FIG. 5 schematically illustrates a flexible mycological composite material produced in accordance with the invention in a partially unrolled condition; and FIG. 6 schematically illustrates an initial step in a heat and compression process during the further processing of the mycological composite material of FIG. 5;

FIG. 7 schematically illustrates the mycological composite material of FIG. 5 in a heated form during a heat and compression step in accordance with the invention;

FIG. 8 schematically illustrates the mycological composite material of FIG. 5 during removal from the form of FIG. 7; an FIG. 9 illustrates a formed mycelium/substrate product formed in the form of FIG. 7.

FIG. 1 illustrates an image of part of a fungal network of hyphae 10 with a detail of the structure of a fungal cell wall composed of intracellular chitin and structural saccharides shown to the right.

As illustrated in the detail at Right, top, the fungal cell wall has repeat units of the structural polymer chitin, and the deacetylated derivative, chitosan, where the degree of deacetylation (DD), and degree of acetylation (DA) can vary as complimentary fractions between 0-1. As illustrated in the detail at Right, middle, the fungal cell wall has structural sterol commonly found in fungal cell membranes and as illustrated in the detail at Right, bottom the fungal cell wall has repeat units of the structural saccharides β-d (1,3) and (1,6) glucans. Not shown: catechols, hydrophobins, proteins or other more complex structural cell components.

Referring to FIG. 2, the process for the production of mycelial composite surfaces in a roll-to-roll format is performed in accordance with the following steps that can be used alone or in combinations thereof.

First, an inoculum 11 of mycelial tissue is provided at an inoculation station 12. For example, the inoculum 11 may be obtained by growing a growth media as a solid mass which is then ground up to produce particles or pellets with mycelium therein as disclosed in US 2015/0101509.

Second, a substrate of fibrous material 13 is passed under the inoculation station 12 as a travelling web with the inoculum 11 being deposited under gravity onto the surface of the web 13.

Third, the inoculated substrate 13 is rolled into a roll 14 and thereafter incubated for a time sufficient for the mycelial tissue to grow hyphae that enmesh with the substrate by extending around the fibers of the substrate to form a cohesive unified filamentous network with the rolled inoculated substrate being characterized in being flexible.

Alternatively, the incubated substrate 13 may be rolled up with a support web of porous material 15 into a roll of alternating layers of substrate and porous material.

Fourth, in either case, the roll 14 is dehydrated to below 20% moisture and ideally below 8% for storage and/or transportation to another site for further processing. In this condition, the incubated substrate 13 is flexible.

Referring to FIG. 3, wherein like reference characters indicate like parts as above, the process of FIG. 2 may be modified by employing a liquid inoculum spray 16 in the inoculation station 12 for deposition of the inoculum 16 on a surface of the substrate 13.

Referring to FIG. 4, wherein like reference characters indicate like parts as above, the process of FIG. 2 may be modified by employing a bath of inoculum 17 in the inoculation station 12 for passage of the web of substrate 13 therethrough.

As indicated in FIG. 3, pairs of rollers 18, 19 are provided for conveying the web of substrate 13 through the inoculation station 12, preferably under a slight tension, and guide rollers 20 are provided for guiding the substrate 13 through the bath of inoculum.

Referring to FIG. 5, the substrate of fibrous material 13 may be selected from a woven substrate 13' or a non-woven substrate 13" and, where used, the support web of porous material 15 may be selected form a plastic porous membrane 15', a plastic mesh or similar 15" and a plastic corrugate or similar 15'''.

The particulars of the process steps are as follows:

1. Substrate selection, use one or more of the following materials, in combination or concert, as substrate or additional material to existing myceliated material: 1 grams/square meter to 100 kg/square meter of fibrous material deemed appropriate:
    a. Flexible agricultural waste fibers
    b. Non-flexible agricultural fibers
    c. Lignocellulosic fibers
    d. Sugar fibers
    e. Cellulosic fibers
    f. Lignin fibers
    g. Hemicellulose (fibrous form)
    h. Xylose (fibrous form)
    i. Electrospun cellulosic or lignocellulosic fibers
    j. Electrospun cellulosic or lignocellulosic fibers on a synthetic support
    k. Solvent (and/or salt) spun or extracted cellulosic or lignocellulosic fibers
    l. Solvent (and/or salt) spun or extracted cellulosic or lignocellulosic fibers on a synthetic support
    m. Non-woven lignocellulosic fibers on a synthetic support
    n. Woven lignocelluosice fibers on/in a lignocellulosic support
    o. Lignocellulosic fibers woven into synthetic support
    p. Entangled lignocellulosic fibers (Hydro, needle-punched, or other mechanical process) fibers on synthetic or natural fiber or particle support
    q. Combination of the like
2. Prepare Substrate material for inoculation using one or more of the following:
    a. Steam
    b. Heat
    c. Pressure
    d. $H_2O_2$
    e. Acid sterilization
    f. Base sterilization
    g. UV/Ebeam
    h. Boiled (roll to roll or batch autoclaved)
    i. PEO sterilized (e.g. cinnemaldehyde)
    j. Co-habitation with other species, or spores
    k. Pre-digested by other organisms
    l. No preparation used, i.e. raw
    m. Combination of the like
3. Use one or more of the following inoculation media or methods to introduce organism binder to mat/fibrous material in order to generate biological resin.
    a. Pre-inoculated, unaltered grain/millet spawn particle form distributed onto substrate by deposition or conveyance b. Pre-inoculated grain/millet spawn particle in altered size/aspect ratio by mechanical process, distributed onto substrate by deposition or conveyance
c. Pre-inoculated grain/millet spawn particle in altered size/aspect ratio by mechanical process, filtered and distributed onto substrate by deposition or conveyance
d. Fibrous substrate grown in contact with surface of adjacent pre-inoculated material
e. Suspended/distributed tissue, cultured and placed onto substrate without co-conveyance of pre-inoculated material.
f. Ground fibers or particulates pre-inoculated with mycelium to form a batting during incubation
g. Spores (sexual or asexual, cohabitating or compatible) or suspended spores
h. Combination of reproductive and vegetative mycelial tissue distributed onto substrate by deposition or conveyance
i. Spores and/or tissue with added nutrition, in solution or solid form.
j. Ground fibers or particulates pre-inoculated with mycelium to form a batting during incubation.

Nutrition may be added as an option with the amount of added nutrition ranging from no additive (0 g) to 25% by mass of substrate mat or pre-matted fiber/particle) material. If added, the nutrition may be selected from:
  i. Grain, flours, minerals, starches, proteins
    a. Clear flour
    b. maltodextrin
    c. Wheat bran
    d. Algae
    e. Yeast
  ii. Nutrition can be liquid and/or suspension (dilute to semi-dilute regime)
  iii. Nutrition can be paste (ranging from Newtonian fluid, viscous suspension, semi-dilute suspension, concentrated suspension, viscoelastic paste, gel)
    1. No additive
    2. Liquid with additive (natural or synthetic)
      a. Starch, viscosity agent, gelling agent,
    3. Solids diluted or suspended
  k. Combination of the like
4. Mycelial tissue growth to obtain desired biomass content. Use one or the following in combination or concert with the method described in U.S. Pat. No. 8,001,719 for producing rapidly renewable chitinous material.
  a. Incubate
    i. Parameters including, but not limited to:
      1. Temperature (5 C-40 C)
      2. Relative Humidity (10%-100%)
      3. CO2 (0%-20%)
    ii. Physical format
      1. Roll substrate and biomass prior to incubation
        a. Stand-off using synthetic or natural material as a mechanically stable support for substrate material to grow upon in a rolled format, minimizing dimensional instability during colonization (incubation) period
        b. Corrugated sheeting rolled goods
        c. Non-corrugated sheeting
        d. Woven fabrics
        e. Perforated sheeting
        f. Rods/wires/mesh
        g. Screen materials
        h. Combination of the like
        i. Actively aerated
        j. Passively aerated
      2. Sheets, non rolled configuration of 1 above
      3. Lamination: Allow fungal tissue to grow and penetrate into/from:
        a. Adjacent mat material
        b. Adjacent particulate material
        c. Synthetic material
        d. Material with competing/cohabitating organism
    iii. Preconfigured shape
      1. Preformed in dimensions near net to final product dimensions
      2. As predetermined shape optimal for pressing/rolling/dehydrating/shipping Referring to FIGS. 6 to 9, in order to process the roll 14 of inoculated substrate into a final product, use is made of a heat and compression apparatus 21, such as described in US 2015/0101509.

As indicated in FIG. 5, a length of the incubated substrate is unrolled from the rolled substrate 14 and placed between two mold forms 22, 23 of the apparatus 21. The lower mold form 23 has a protrusion 24 and the upper mold form 22 has a mating cavity (not shown) in order to form the substrate into a desired shape.

Thereafter, as indicated in FIG. 6, the mold forms 22, 23 are closed on the length of substrate 14 and the substrate 14 is subjected to heat and pressure sufficient to cause the glucan-containing mycelial cells therein to bond the length into a rigid structure 25 as indicated in FIG. 8.

After opening of the mold forms 22, 23 from each other as indicated in FIG. 8, the rigid structure 25 which conforms to the shape of the mold cavity of the apparatus 21 is removed.

As indicated in FIG. 9, the rigid body 25 is of a rectangular shape with a truncated trapezoidal projection and has a thickness that may be uniform throughout depending on the clearances between the mold forms 22, 23.

The particulars of the process steps for processing of the inoculated substrate roll 14 are as follows:
  5. Dehydrate proliferated mycelial/lignocellulosic material, if necessary or desired, to below 20% moisture by mass and ideally below 8%.
    a. Rehydrate up to 30% to 70% moisture depending on substrate to re-animate tissue
      i. Follow desired (or combination) of curing steps in section 6
    b. Steam during pressing to activate glucans and other intra/extracellular compounds:
      i. Use existing channels in platen
      ii. Introduce a hydrated layer to fuse
      iii. Introduce a hydrated layer to be delaminated
      iv. Use high, or low vapor pressure solvents to control vapor release
      v. Use chemical agents to deteriorate or enhance physical crosslinking
      vi. Use a biomimecry process to induce mineralization or other naturally occurring process
        1. Use heat/agitation/energy source or pressure to accelerate (or decelerate chemical or biological process)
        2. Use cold or heat transfer to control thermodynamics and kinetics
      vii. Use a second, third, or subsequent organism to enhance network fusing through delivered exudate, or vapor 6. Select one or more of the following methods of curing (or the like) to the fungal colonized, uncolonized, or colonized and dehydrated mat material
   a. Non-heated compression (e.g. compacting)
   b. Heated (25 C-2000 C)
   c. Pressing flat (0.1-1,000,000 psi)
      i. Single open-press
      ii. Multi open-press
      iii. Continuous press
      iv. Roller press
      v. Stretching/alignment roller apparatus
      vi. Cooling/treating bath
      vii. Pullout assembly
      viii. Reheating stations
      ix. Integrated (or non-integrated) cutting unit
      x. Integrated coating (pre, or post-curing) of natural or synthetic material to enhance stiffness, flame retardance, antimicrobial, abrasion
   d. Pressing on feature-containing surface (0.1-1,000,000 psi)
   e. Heated pressing flat (0.1-1,000,000 psi)
   f. Heated pressing on feature-containing surface (0.1-1,000,000 psi)
   g. Embossed (heated or non-heated)
   h. Roll to roll drying
   i. Spray coating prior to pressing
      i. Enhance/attenuate adhesion, internal bond strength antimicrobial activity, abrasion resistance, surface finish, modulus, or other like properties
   j. Injected components (solvent, chemical, or the like)
      i. Enhance/attenuate adhesion, internal bond strength, antimicrobial activity, abrasion resistance, surface finish, modulus, or other like properties
   k. Plant essential oils
   l. Dehydrate
   m. Ebeam/UV/radiation
   n. Combination of the like
7. Select one or more of the following feature containing surfaces (or the like) for transferring features to inoculated mat material (cured, or non-cured) [GT=>add as parallel to flow-chart, e.g. bottle type process]
   a. Isobaric transfer of features (constant pressure)
   b. Isochoric transfer (strain controlled)
   c. Incremental pressing,
   d. Embossed features
   e. Roll-to-roll die cutting
   f. Curved surface on single or multi-open press
   g. Flat or curved surface with cutouts stamped into
   h. Combination of the like It should be noted that all chemical modifications (naturally, synthetically, or enzymatically derived) may be executed in variant levels of functionality (i.e. substitutions may range from 0 to 1 to 2 or higher), e.g. bifunctional or higher to involve reactive steps intra or inter-cellular biomolecule chain linking to impart targeted chemical modification characteristics, and additionally effect network structure and performance, and subsequently bulk material properties.

The following is an example of making a rolled composite in accordance with the invention.

EXAMPLE

Preparation of Inoculated Hemp Mat Material Using a Grain Spawn Slurry Inoculum

1. Aseptically, combine grain spawn in a blended with sterile water at a rate of 2:1
2. Blend material for 90 seconds until the grains have been mechanically disrupted and have the appearance of a paste ("inoculum concentrate")
3. In an aseptic vessel of sufficient size: Adjust the volume of inoculum concentrate with additional sterile water to yield the desired quantity and inoculation rate. Additional nutrients as described in the above list (flour, wheat bran, etc.) may also be mixed in at this step. This process yields a bath of "working inoculum".
4. Introduce a sanitized (via a 60min soak in 10% hydrogen peroxide) hemp mat material into the bath of working inoculum using a set of rollers to remove excess residual hydrogen peroxide.
5. Once mat has had as little as 2-10 seconds of dwell time in the inoculum bath, the mat is removed by being passed through a second set of sanitary rollers. These rollers remove the excess inoculum liquid, which may be reclaimed for further processing. (note: in practice, this brief dwell time may be regarded as a continuous passing of mat through the inoculum bath.)
6. As the mat is conveyed out of the bath and through the rollers, the may be rolled continuously onto a spool of rigid plastic or other solid support. To do this efficiently, this process is executed synchronously with a solid support being unrolled to form a "roll to roll" product.
7. The completed roll of material is placed in a suitable incubation environment to maintain temperature and RH amernable to the organism with which the material was inoculated for the duration of growth.
8. The fully colonized mat (on the order of 4-20 days of incubation, highly dependent on the species, substrate, and nutrition used) may be stored.
9. Completed mat may be dried and dehydrated to use in a low-density format. The completed mat may also be processed with heat and pressure to yield a higher density rigid biocomposite.

The invention thus provides a relatively simple process for the production of mycelial composite surfaces in a roll-to-roll format as well as a mycological composite in rolled format.

The invention further provides a mycological composite in rolled format. that can be unrolled and subjected to heat and pressure to make rigid mycological products.

What is claimed is:

1. A method of producing a mycological composite material comprising
   forming an inoculum of mycelial tissue;
   inoculating a substrate of fibrous material with said inoculum;
   rolling the inoculated substrate into a roll; and
   thereafter incubating the rolled inoculated substrate for a time sufficient for the mycelial tissue to grow hyphae; said hyphae enmeshes with the substrate by extending around the fibers of the substrate to form a cohesive unified filamentous network;
   the rolled inoculated substrate being flexible.

2. A method as set forth in claim 1 wherein said step of inoculating includes deposition of said inoculum on a surface of the substrate.

3. A method as set forth in claim 2 wherein said step of inoculating includes conveying the substrate during deposition of said inoculum on the surface of the substrate.

4. A method as set forth in claim 1 wherein said step of inoculating includes conveying the substrate through a bath of said inoculum.

5. A method of producing a mycological composite material comprising
forming a bath of mycelial tissue;
conveying a substrate of fibrous material through said bath to inoculate the substrate with mycelial tissue;
rolling the inoculated substrate into a roll; and
thereafter incubating the rolled inoculated substrate for a time sufficient for the mycelial tissue to grow hyphae; said hyphae enmeshes with the substrate by extending around the fibers of the substrate to form a cohesive unified filamentous network;
the rolled inoculated substrate being flexible.

6. A method as set forth in claim 5 wherein said mycelial tissue contains chitin and glucan-containing mycelial cells.

7. A method as set forth in claim 6 further comprising the steps of unrolling a predetermined length of the incubated substrate from the rolled substrate and thereafter subjecting said length to heat and pressure sufficient to cause the glucan-containing mycelial cells therein to bond said length into a rigid structure.

8. A method as set forth in claim 5 further comprising the steps of rolling the incubated substrate with a support web of porous material into a roll of alternating layers of substrate and porous material and dehydrating the rolled substrate to below 20% moisture.

9. A method as set forth in claim 8 further comprising the step of passing a flow of moisture through said layers of porous material into said layers of substrate to re-hydrate said layers of substrate to between 30% and 70% moisture.

10. A method as set forth in claim 8 further comprising the step of unrolling a predetermined length of the incubated substrate and support web from the rolled substrate and thereafter passing a flow of steam through said layers of porous material into said layers of substrate while simultaneously compressing said length to cause the glucan-containing mycelial cells therein to bond said length into a rigid structure.

11. A mycological composite material comprising a web of fibrous material characterized in having mycelial tissue throughout said material with hyphae thereof extending around fibers of the fibrous material to form a cohesive unified filamentous network and wherein said mycelial tissue contains chitin and glucan-containing mycelial cells.

12. A mycological composite material as set forth in claim 11 wherein said web is in a roll and has a web of porous material disposed in alternating layers with said web of fibrous material.

13. A mycological composite material as set forth in claim 11 characterized in being flexible.

14. A mycological composite material as set forth in claim 11 characterized in being rigid and having said chitin and glucan-containing mycelial cells forming crosslinks throughout said material.

15. A mycological composite biomaterial comprising
a first material inoculated with an inoculum of mycelial tissue;
a second material in contact with a surface of the inoculated first material; and
hyphae extending from the inoculated first material and penetrating into and enmeshing with the second material.

16. A mycological composite biomaterial as set forth in claim 15 wherein said first material is made of fibrous material and said inoculum contains chitin and glucan-containing mycelial cells.

17. A mycological composite biomaterial as set forth in claim 16 wherein said second material is a fibrous substrate.

18. A mycological composite biomaterial as set forth in claim 16 characterized in having been subjected to heat and pressure sufficient to cause the glucan-containing mycelial cells therein to bond said mycological composite biomaterial into a rigid structure.

* * * * *